United States Patent
Tian et al.

(10) Patent No.: US 8,781,196 B2
(45) Date of Patent: Jul. 15, 2014

(54) METHODS AND SYSTEMS FOR DEFINING A VOI IN AN ULTRASOUND IMAGING SPACE

(75) Inventors: Yong Tian, Shenzhen (CN); Bin Yao, Shenzhen (CN)

(73) Assignee: Shenzhen Mindray Bio-Medical Electronics Co., Ltd, Shenzhen (CN)

( * ) Notice: Subject to any disclaimer, the term of this patent is extended or adjusted under 35 U.S.C. 154(b) by 784 days.

(21) Appl. No.: 12/951,935

(22) Filed: Nov. 22, 2010

(65) Prior Publication Data

US 2011/0129137 A1    Jun. 2, 2011

(51) Int. Cl.
| | | |
|---|---|---|
| G06K 9/00 | (2006.01) | |
| G06T 7/00 | (2006.01) | |
| G01S 7/52 | (2006.01) | |
| G06T 19/00 | (2011.01) | |
| A61B 8/00 | (2006.01) | |
| G01S 15/89 | (2006.01) | |

(52) U.S. Cl.
CPC ....... G01S 7/52063 (2013.01); *G06T 2219/008* (2013.01); *A61B 8/466* (2013.01); *G06T 2207/10132* (2013.01); G06T 7/0081 (2013.01); *G01S 15/8993* (2013.01); G06T 19/00 (2013.01); *G06T 2207/20104* (2013.01); *A61B 8/469* (2013.01)
USPC .......................................... 382/131; 382/190

(58) Field of Classification Search
CPC .... A61B 8/461; A61B 8/466; G01S 15/8993; G01S 7/52063; G06T 19/00
USPC .................. 382/128–131, 154, 190, 264, 275; 600/407, 440, 441, 443, 447
See application file for complete search history.

(56) References Cited

U.S. PATENT DOCUMENTS

| | | | | |
|---|---|---|---|---|
| 5,555,352 | A * | 9/1996 | Lucas | 345/423 |
| 5,995,580 | A * | 11/1999 | Schaller | 378/15 |
| 7,433,504 | B2 * | 10/2008 | Deischinger et al. | 382/128 |
| 7,447,341 | B2 * | 11/2008 | Karau et al. | 382/128 |
| 7,471,815 | B2 * | 12/2008 | Hong et al. | 382/128 |
| 8,009,887 | B2 * | 8/2011 | Ionasec et al. | 382/128 |
| 8,081,807 | B2 * | 12/2011 | Xu et al. | 382/128 |
| 8,447,383 | B2 * | 5/2013 | Hyun et al. | 600/427 |
| 8,457,435 | B2 * | 6/2013 | Zou et al. | 382/264 |
| 2003/0083578 | A1 * | 5/2003 | Abe et al. | 600/447 |
| 2003/0210811 | A1 * | 11/2003 | Dubowsky et al. | 382/128 |
| 2004/0081340 | A1 * | 4/2004 | Hashimoto | 382/128 |
| 2005/0090743 | A1 * | 4/2005 | Kawashima et al. | 600/443 |
| 2005/0240104 | A1 * | 10/2005 | Shim et al. | 600/437 |
| 2005/0251066 | A1 * | 11/2005 | Mack | 600/590 |
| 2006/0257009 | A1 * | 11/2006 | Wang et al. | 382/128 |

(Continued)

FOREIGN PATENT DOCUMENTS

| | | |
|---|---|---|
| CN | 101088468 A | 12/2007 |
| CN | 101292883 A | 10/2008 |
| EP | 1973076 A1 | 9/2008 |

*Primary Examiner* — Chan Park
*Assistant Examiner* — Mia M Thomas
(74) *Attorney, Agent, or Firm* — Kory D. Christensen; Stoel Rives LLP (57) ABSTRACT

An ultrasound imaging system provides for defining a VOI in an ultrasound imaging space. The system defines an initial frame of the VOI in the ultrasound imaging space, receives a selection of at least one reference point at an arbitrary location in the ultrasound imaging space, creates at least one curved surface using at least one element of the initial frame and the at least one reference point, and then creates VOI based on the curved surface in the ultrasound imaging space.

16 Claims, 8 Drawing Sheets

(56) References Cited

U.S. PATENT DOCUMENTS

| | | | |
|---|---|---|---|
| 2007/0038065 A1* | 2/2007 | Creighton et al. | 600/407 |
| 2007/0038085 A1* | 2/2007 | Zhang et al. | 600/437 |
| 2007/0052700 A1* | 3/2007 | Wheeler et al. | 345/419 |
| 2007/0255139 A1* | 11/2007 | Deschinger et al. | 600/443 |
| 2008/0101672 A1* | 5/2008 | Matsumoto | 382/128 |
| 2008/0170765 A1* | 7/2008 | D'sa et al. | 382/128 |
| 2008/0267467 A1* | 10/2008 | Sokulin et al. | 382/128 |
| 2008/0291396 A1* | 11/2008 | Baer et al. | 351/211 |
| 2009/0062646 A1* | 3/2009 | Creighton et al. | 600/437 |
| 2009/0123050 A1* | 5/2009 | Ionasec et al. | 382/131 |
| 2009/0306507 A1* | 12/2009 | Hyun et al. | 600/443 |
| 2010/0149139 A1* | 6/2010 | Kroll et al. | 345/204 |
| 2010/0292574 A1* | 11/2010 | Hyun et al. | 600/443 |
| 2011/0129137 A1* | 6/2011 | Tian et al. | 382/131 |
| 2011/0299755 A1* | 12/2011 | Zou et al. | 382/131 |
| 2012/0184851 A1* | 7/2012 | Arai et al. | 600/443 |
| 2013/0006108 A1* | 1/2013 | Yoshiara et al. | 600/431 |
| 2013/0150717 A1* | 6/2013 | Sato | 600/441 |
| 2013/0165784 A1* | 6/2013 | Kim et al. | 600/441 |

\* cited by examiner

Reference Plane

FIG. 14 ated States Patent

US 8,781,196 B2

METHODS AND SYSTEMS FOR DEFINING A VOI IN AN ULTRASOUND IMAGING SPACE

CROSS-REFERENCE TO RELATED APPLICATIONS

This application claims the benefit of Chinese Patent Application No. 200910225716.0, filed on Nov. 27, 2009, which is incorporated herein by reference.

TECHNICAL FIELD

The following disclosure relates generally to three-dimensional (3D) ultrasound imaging systems, and more particularly to methods and systems for defining a volume of interest (VOI) in an ultrasound imaging space.

BACKGROUND

Ultrasound imaging devices are widely used because they are non-destructive, radiationless, and highly flexible in operation. Conventional ultrasound imaging devices provide only two-dimensional images of the human body. Therefore, the sizes and shapes of lesions can only be empirically estimated by doctors based on a plurality of two-dimensional images, and the three-dimensional geometry of a lesions and its surrounding tissues must be imagined by the doctor. This leads to difficulties in diagnosis.

With the application of 3D visualization technology in ultrasound imaging systems, diagnosis has become more convenient. For example, a 3D image may be reconstructed base on a series of two-dimensional images and then may be displayed on a monitor. Not only the overall visual construction of the imaging object may be obtained from the 3D image, but also a lot of important 3D information may be saved. As a result, 3D ultrasound imaging devices have been widely used in clinical practice in recent years.

The 3D ultrasound imaging process usually includes three steps: data acquisition, reconstruction and rendering. 3D ultrasound volume data are collected in the data acquisition step. In the reconstruction step, the collected volume data are converted to corresponding volume data in Cartesian coordinates. To obtain an accurate and undistorted 3D image, the relative position of the volume data in Cartesian coordinates must be consistent with the real space position of the volume data. In the rendering step, the volume data are calculated using a visualization algorithm to obtain visual data, after which the visual data are displayed on a monitor.

In order to obtain more effective 3D rendering, 3D ultrasound systems typically use VOI (volume of interest) technology. The VOI represents a user-configurable geometric figure in three-dimensional space. Using the VOI in 3D rendering, only the volume data inside the geometric figure are used to produce a 3D image. The volume data in which users are interested are defined as the target, while the other data are defined as the background. If the users can make the target into the VOI, then only the 3D image of the target is obtained and displayed. Thus, VOI technology facilitates target observation.

Traditional VOI is preset as a rectangular parallelepiped that includes 6 flat surfaces. This can easily lead to ineffectiveness of separating the target and the background when the target profile is complicated. If at least one of the flat surfaces is replaced by a "curved" surface, it is referred to as a curved surface VOI. The curved surface VOI greatly increases the flexibility of the VOI setting, making it easier for users to separate the target and background based on objective conditions or subjective personal ideas.

U.S. Pat. No. 7,433,504 discloses a method for defining a volume of interest in a medical image. According to this method, a user interface is used to select a point on an initial linear border segment of a VOI. The user then moves the point from its initial position on the linear border segment to a new position and a processor then forms a new, non-linear border segment that includes the point. A 3-D presentation of the VOI is then created.

SUMMARY

An ultrasound imaging system according to one embodiment provides method for defining a VOI in an ultrasound imaging space. The system defines an initial frame of a VOI in ultrasound imaging space, receives a selection of at least one reference point at an arbitrary location in the ultrasound imaging space, creates at least one curved surface using at least one element of the initial frame and the at least one reference point, and then creates the VOI based on the curved surface in the ultrasound imaging space.

DETAILED DESCRIPTION

Figure 1:
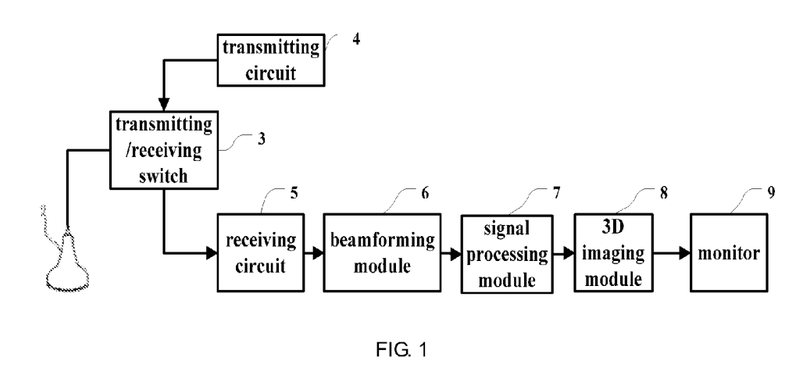
FIG. 1 is a block diagram of an embodiment of a 3D ultrasound imaging system.

Referring to FIG. 1, in certain embodiments, a 3D ultrasound imaging system includes a probe 2, a transmitting/receiving switch 3, a transmitting circuit 4, a receiving circuit 5, a beam-forming module 6, a signal processing module 7, a 3D imaging module 8, and a monitor 9. The transmitting circuit 4 sends a group of pulses which have been focused with time delays to the probe 2. The probe 2 emits ultrasound waves to the tissues to be imaged (not shown), then receives ultrasound echoes reflected from the tissues which carrying tissue information, and converts the ultrasound echoes to electrical signals. The receiving circuit 5 receives these electrical signals and transmits them to the beam-forming module 6. After time delay focusing, weighting and channel summation processing, those signals are transmitted to the signal processing module 7 for signal processing. Thereafter, the signals are sent to the 3D imaging module 8 for 3D imaging processing. Finally, the 3D images with other visual information are transmitted to the monitor 9 for display.

Figure 2:
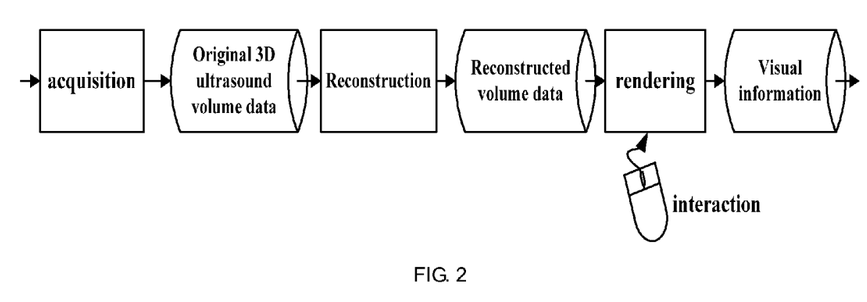
FIG. 2 is a flow-chart illustrating a 3D imaging process according to the 3D ultrasound imaging system of FIG. 1.

As shown in FIG. 2, a processing procedure of the 3D imaging module 8 includes three steps: acquisition, reconstruction and rendering. In the acquisition step, the original 3D ultrasound volume data are obtained. There are typically two ways to obtain the original 3D volume data. The first is using free hand scanning, and acquiring the 3D volume data offline. The second is using a special volume-scanning probe, which can obtain real-time 3D volume data.

In the reconstruction step, the original volume data are converted into reconstructed volume data in some chosen coordinate system, such as rectangular, Cartesian coordinates, which have relative positions corresponding to that of the real space. Thus, in the rendering step, accurate images without distortion can be obtained.

In the rendering step, the reconstructed volume data are processed with a visual algorithm to obtain visual information (e.g., 3D images), and the visual information is displayed on a monitor.

The original volume data are acquired in the acquisition step, then the original volume data are converted into reconstructed volume data in the reconstruction step, and the reconstructed volume data are calculated and processed with possible user's interaction to obtain the visual information.

In the 3D ultrasound imaging process, typically the entire space region is scanned including the imaging target to obtain the information about the tissue or other targets (organs, blood, etc.) in the target space region. The space region is referred to herein as the "ultrasound imaging space".

In order to carry out 3D rendering more effectively, 3D ultrasound systems use VOI technology. By using the VOI technology, a geometric figure is defined in the ultrasound imaging space. In the 3D rendering step, only the volume data which are contained in this geometric figure (VOI) will be rendered in conventional systems.

Figure 3:
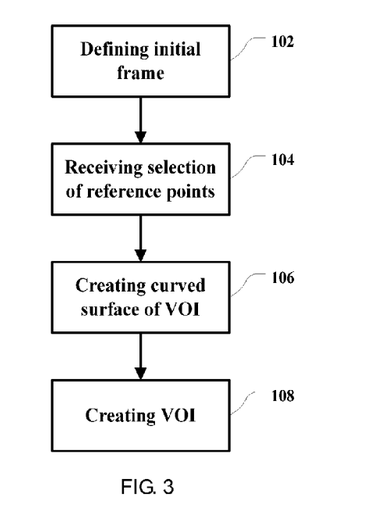
FIG. 3 is a flow diagram of an embodiment of a method for defining a VOI.

As shown in FIG. 3, a method for defining a VOI includes an initial frame definition step 102, a reference point selection step 104, a VOI curved surface generation step 106, and a VOI creation step 108.

The VOI may be defined without showing the ultrasound images. In addition, the VOI can also be adjustable for users, and users' interactions may be included in the process of defining the VOI. Therefore, it is feasible to display the ultrasound image, and define the VOI, according to the displayed ultrasound image. As a result, it is possible to see whether the desired 3D imaging target is included in the defined VOI. Certain embodiments may also include steps of displaying ultrasound images.

In the initial frame definition step 102, an initial frame of the VOI is defined in the ultrasound imaging space as the basis of the final VOI. The initial frame may be one of the common geometric figures, such as cuboid, cube, cylinder, etc., and could be chosen based on actual needs, taking into account such factors like convenience of subsequent calculations. Setting of the initial frame, including its shape, size, location in the image, etc., may be set with default settings during the initialization of the 3D ultrasound imaging system, and may also be set by the user through a user interface. The set initial frame may also be adjusted by the user through the user interface or automatically by the 3D ultrasound imaging system. The set initial frame may include the whole 3D imaging target, part of the 3D imaging target, or even exclude the 3D imaging target.

Figure 4:
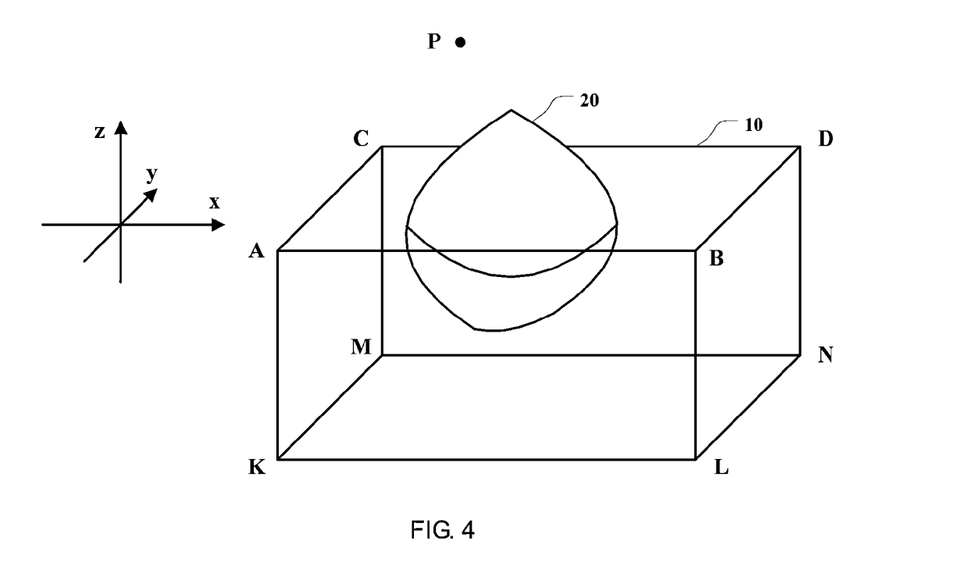
FIG. 4 is a schematic diagram of an embodiment of a initial frame of a VOI.

In one embodiment, the initial frame is set to be a cuboid as shown in FIG. 4. In this embodiment, the 3D imaging target 20 is not totally contained in the initial frame 10.

In the reference point selection step 104, at least one reference point is selected from the ultrasound imaging space according to a received reference point selecting signal. The location of this reference point may be anywhere in the ultrasound imaging space, including the inside of the initial frame or outside of the initial frame. The reference point selecting signal may be a default setting from the 3D ultrasound imaging system, which gives the 3D coordinates of the reference point(s) directly. Alternatively, it may be inputted via a user interface. For example, the 3D coordinates of the reference points may be entered into the system directly, or by moving a mouse to position two of the coordinates x, y, and z, while rotating the mouse wheel to position the other one. There may be one reference point, or more. It is based on actual needs of imaging and may be chosen flexibly. An example of selecting a reference point is shown in FIG. 4, in which point P is the selected reference point.

In the VOI curved surface generation step 106, the reference point(s) selected in step 104 and at least one element of the initial frame are used to generate at least one curved surface. The "element" of the initial frame herein refers to the point or line segment (straight or curved) of the initial frame. Here the "curved surface" includes a surface constituted by planes, that is, a surface constituted by planes is regarded as a special case (curvature=0) of a curved surface in this disclosure.

With the reference points and the elements of the initial frame, there may be many methods to generate the curved surface of VOI, and those methods may be selected according to the actual situation. The following are examples of the method for generating a curved surface of the VOI.

FIG. 4 shows one example. For facilitating the expression and calculation of the curved surface of the VOI, the initial frame 10 may be set to be a cuboid, and an end plane ABCD of the initial frame 10 may be parallel with the xy plane and the edges of end plane ABCD may be parallel with the x axis or y axis respectively. If the direction of the end plane ABCD does not meet the aforementioned feature, a step of a coordinate transformation may be applied to move the end plane ABCD to the desirable direction. This rule will be adopted in the following descriptions, and the positive direction of the axes x, y, and z may be regarded as the direction of right, up, and forward, respectively, and the contraries may be regarded as direction of left, down, backward, respectively.

Figure 5:
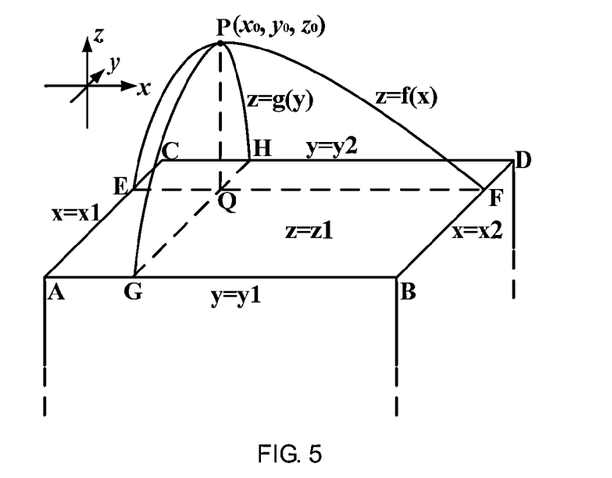
FIG. 5 is a schematic diagram illustrating an embodiment of generating a curved surface of a VOI base on the initial frame and the reference point.

With reference to FIG. 5, assume that coordinates of each apex of the rectangle ABCD are $A(x_1,y_1,z_1)$, $B(x_2,y_1,z_1)$, $C(x_1,y_2,z_1)$, and $D(x_2,y_2,z_1)$ respectively. In this disclosure, these apexes are regarded as the feature points of the initial frame. Assume the coordinates of the reference point P are $(x_0,y_0,z_0)$. On this basis, several auxiliary points, such as projection points, may be obtained. For example, drawing a line starting from the reference point P and perpendicular to the surface on which the rectangle is located, the foot point $Q(x_0,y_0,z_1)$ is the projection point on the surface of the reference point P. For another example, drawing four lines which start from the point Q and are perpendicular to the four edges of the rectangle ABCD respectively, the foot points $E(x_1,y_0,z_1)$, $F(x_2,y_0,z_1)$, $G(x_0,y_1,z_1)$ and $H(x_0,y_2,z_1)$ may be regarded as the projection points on the initial frame of the reference point P.

In one embodiment, the curved surface of the VOI may be simply as a pyramid which has the reference point P as the vertex and the four edges AB, BD, DC and AC of the rectangle as the base lines.

In other embodiments, the curved surface of the VOI may be an algebraic surface defined by the reference points and at least one point on the initial frame. For example, a paraboloid may be used which employs the reference point P as the vertex and passes through four points E, F, G and H on the initial frame, or a paraboloid which employs the reference point P as the vertex and passes through four points A, B, C and D, or a hyperboloid which employs the reference point P as the vertex and passes through four points E, F, G and H, or a hyperboloid which employs the reference point P as the vertex and passes through four points A, B, C and D, or a ellipsoid which employs the reference point P as the vertex and passes through four points E, F, G and H, or a ellipsoid which employs the reference point P as the vertex and passes through four points A, B, C and D, may be selected as the curved surface of the VOI. Other examples are: a hyperboloid of rotation or a paraboloid of rotation which employs the reference point P as the vertex and pass through two points E and F; a hyperboloid of rotation or a paraboloid of rotation which employs the reference point P as the vertex and pass through two points G and H; a hyperboloid of rotation or a paraboloid of rotation which employs the reference point P as the vertex and pass through two points A and D; a hyperboloid of rotation or a paraboloid of rotation which employs the reference point P as the vertex and passes through two points B and C; a cone surface or truncated cone surface which employs the reference point P as the vertex and passes through at least one point of the A, B, C, D, E, F, G, and H. A polynomial curved surface which passes through the reference point P and one or more points of the aforementioned points A, B, C, D, E, F, G, and H may also be served as the curved surface of the VOI, and these exemplary points A, B, C, D, E, F, G, and H may be replaced by other points on the line segments AB, BD, DC and AC.

The manner in which the curved surfaces are generated may be set by default settings of the 3D ultrasound imaging system, as well as the user's input through the user interface according to the actual needs. When the manner of generating curved surfaces of the VOI is determined, as the coordinates of the points P, A, B, C, D, E, F, G, and H are known or may be calculated, the equation of the curved surfaces of the VOI may be obtained based on these coordinates according to known mathematical methods. Thus, the curved surfaces of the VOI are determined.

In another embodiment, a method for calculating the curved surface of the VOI includes the steps of: calculating projection points of the reference point in the initial frame along at least two directions; calculating curves defined by the reference point and the projection points along each direction respectively to obtain at least two interim curves; and calculating synthesized curved surfaces based on at least two of the interim curves. Thus, the synthesized curved surface may serve as the curved surface of the VOI.

As shown in FIG. 5, projection points E and F of the reference point P on the initial frame work along the direction parallel with the axis x and projection points G and H along the direction parallel with the axis y are initially calculated. After that, two space curves EPF and GPH which pass through the reference point P may be calculated as the interim curves. A skilled artisan will understand that the directions along which the point P is projected may be arbitrary. The number of directions may be more than two and more than two interim curves may be obtained accordingly. The angle between the directions may be chosen flexibly according to actual needs, and may not limited to 90 degrees.

To facilitate the calculation, the plane in which the space curves EPF is located is parallel with the plane defined by the x and z axes, and the plane in which the space curves GPH is located is parallel with the plane defined by the y and z axes. Therefore, the curve EPF may be calculated within the plane xz, and the y coordinate of the points involved may be ignored. Accordingly, the coordinates of the three points E, P, and F may be marked as $E(x1, z1)$, $P(x0, z0)$, and $F(x2, z1)$ respectively. Similarly, the points G, P, and H may be marked as $G(y1, z1)$, $P(y0, z0)$ and $H(y2, z1)$ respectively. Accordingly, the calculating of the space curves may be regarded as the problem of defining a curve through three arbitrary points in a plane. There are various methods for calculating the space curves EPF and GPH, which may be chosen or set according to actual needs. The following are non-restrictive examples of the method for calculating the space curves EPF and GPH.

First, a curve may be drawn which employs the point P as the vertex and pass through the other two points, such as a parabola, a hyperbola, an elliptical curve, etc, or any other polynomial curve.

Second, taking the point P as the starting point, at least two sub-curves may be drawn which pass through the other two points respectively. These sub-curves meet each other at the point P. The sub-curves may be a spline curve, an algebraic curve or other types of curves. In this disclosure, a straight line is regarded as a special case (curvature=0) of a curve, and the sub-curves may be a straight line in this embodiment. The sub-curves may be in communication with form a smooth curve (having a defined first derivative at every point) at the point P, as well as a non-smooth curve.

According to the aforementioned methods, the curve EPF is calculated in the plane xz and marked with an equation $z=f(x)$, and the curve GPH is calculated in the plane yz and marked with an equation $z=g(y)$. Calculating the equation of a certain type of curve base on some known points is a known mathematical process and will not be discussed in detail herein.

The obtained interim curves EPF and GPH may then be used to calculate the synthesized curved surface. There are many methods for calculating a synthesized curved surface according to at least two known curves, which may be chosen according to actual needs. In this embodiment, two exemplary methods for calculating a synthesized curved surface are described hereafter.

Method 1: A equation of the curved surface may be determined base on the interim curves EPF and GPH according to the following equation:

$$z = \begin{cases} \min(f(x), g(y)) \ldots z_0 > z_1 \\ \max(f(x), g(y)) \ldots z_0 < z_1 \\ z_1 \ldots z_0 = z_1 \end{cases} \quad (2)$$

In equation (2), z0 stands for the z coordinate of the reference point P, z1 stand for the z coordinate of the end plane ABCD. As mentioned above, the end plane ABCD is parallel with the xy plane.

Figure 6:
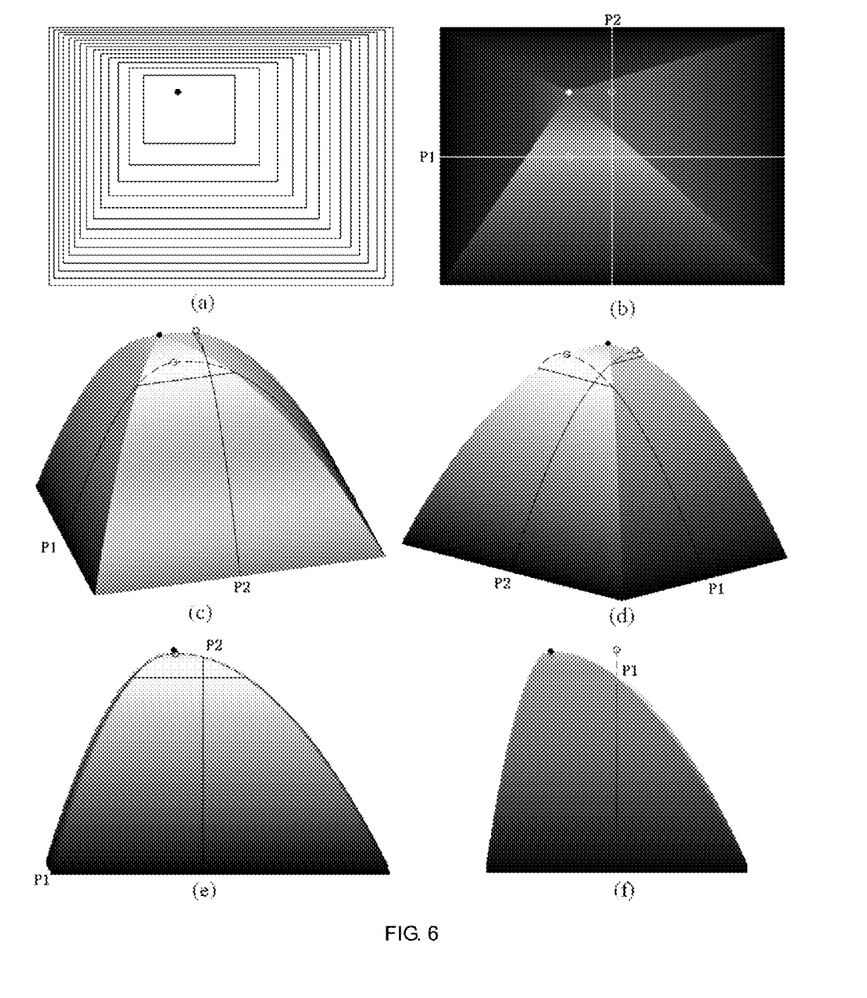
FIG. 6 is a schematic diagram of an embodiment of a generated curved surface of a VOI.

FIG. 6 shows the curved surface obtained. As illustrated, the curved surface is vault shape and is obtained by synthesizing two crossing curves which are in orthogonal planes. This surface is referred to herein as the "orthogonal vault surface". In FIG. 6, the solid point is reference point, the plane P1 and the plane P2 are reference planes (plane P2 is not shown in FIG. 6(e) and FIG. 6(f)), and the hollow points are the projection points of the reference points on the reference planes (described below). FIG. 6(a) is the contour map of the curved surface, the rectangle outside represent the end plane of the initial frame (the end plane ABCD). FIG. 6(b) to FIG. 6(f) show the obtained curved surface stereoscopically, the rectangles at the bottom of which represent the end plane of the initial frame (the end plane ABCD). According to the directions of the coordinate defined by FIG. 5, FIG. 6(a) and FIG. 6(b) represent watching from the front; FIG. 6(c) represents watching from the lower-left-front; FIG. 6(d) represent watching from the lower-right-front; FIG. 6(e) represent watching from below; FIG. 6(f) represent watching from the left. FIG. 6(e) and FIG. 6(f) represent watching from directions which offset at a tiny angle with respect to below or left, not accurately from below or left, by which to improve the stereoscopic feeling of the surfaces.

Method 2: The equation of the curved surface may be obtained according to following equation based on curves EPF: $z=f(x)$ and GPH: $z=g(y)$:

$$z = \begin{cases} \frac{(f(x)-z_1)(g(y)-z_1)}{z_0-z_1} + z_1 & \ldots z_0 \neq z_1 \\ z_1 & \ldots z_0 = z_1 \end{cases} \quad (3)$$

Wherein the z0 is the z coordinate of the reference point, and z1 is the z coordinate of the end plane ABCD.

If the end plane ABCD is defined on the xy plane, that is, z1=0, then, the equation (3) may be simplified as:

$$z = \begin{cases} \frac{f(x)g(y)}{z_0} & \ldots z_0 \neq 0 \\ 0 & \ldots z_0 = 0 \end{cases} \quad (4)$$

Figure 7:
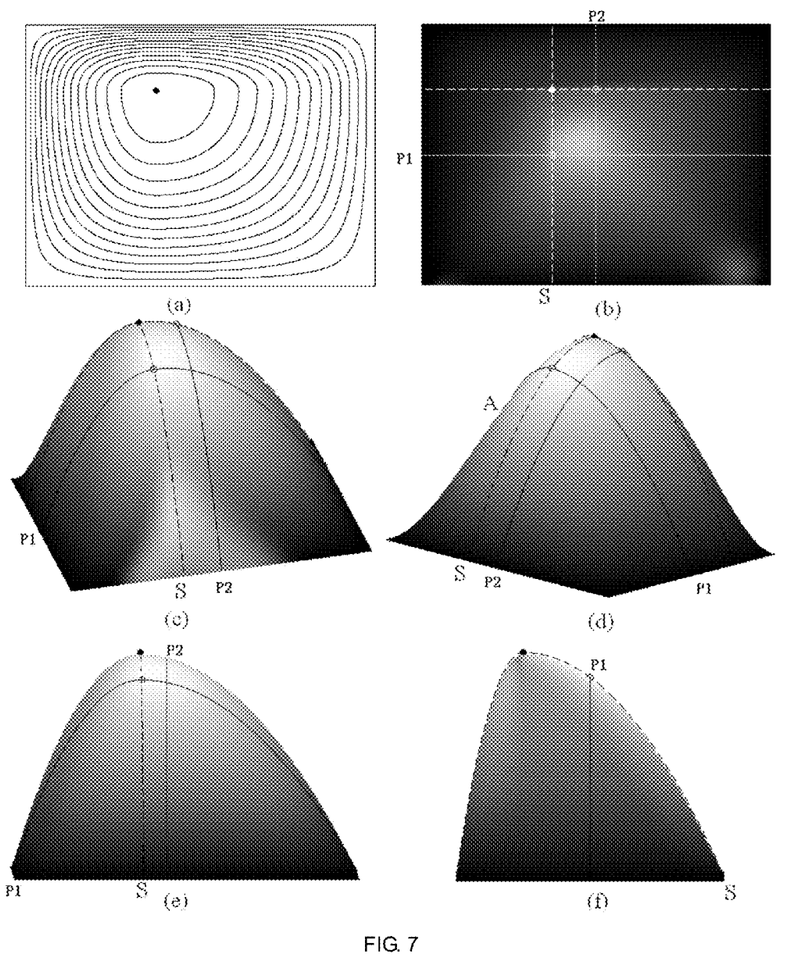
FIG. 7 is a schematic diagram of another embodiment of a generated curved surface of a VOI.

FIG. 7 shows the curved surface of equation (4). This curved surface includes two intermediate curves in two orthogonal planes. This curved surface is referred to herein as the "orthogonal AM surface". The curve S in FIG. 7 is curve GPH. Other points, lines or planes in FIG. 7 are the same as in FIG. 6. The reference point is projected to reference plane P1 along the curve S.

After obtaining the curved surface in step 106, then, in step 108, the VOI may be obtained based on the curved surface.

As shown in FIG. 4, the initial frame 10 is cuboid ABCD-KLMN, which includes six end planes: ABCD, ACKN, AKLB, BLMD, CNMD, KNML. In one embodiment, the end plane ABCD may be replaced by the obtained curved surface described above. This curved surface can form a closed volume together with end planes ACKN, AKLB, BLMD, CNMD, KNML. This closed volume may serve as the expected VOI.

Figure 8:
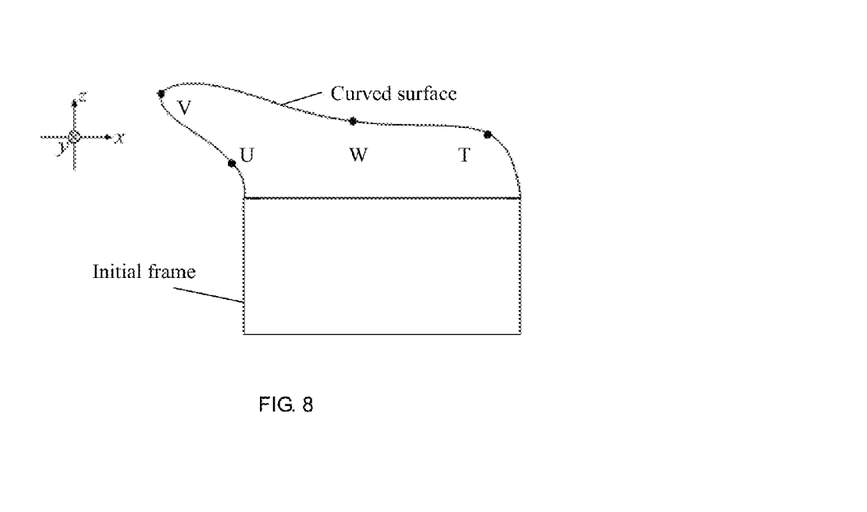
FIG. 8 is a schematic diagram of an embodiment of a plurality of reference points.

In the embodiments described above, the curved surface is obtained based on one reference point. In other embodiments, the curved surface may be obtained based on two or more reference points. FIG. 8 shows the curved surface obtained according to four reference points. The section shown in FIG. 8 is parallel to zx plane. Points T, U, V, W are reference points. In other embodiments, these reference points may be not located on the same section, but on different sections (not shown in FIG. 8).

Similarly, an algebraic surface which passes through these reference points may be created by methods which are similar to those described above, or a synthesized surface may be created by synthesizing two or more surfaces which pass through one or more reference points. This algebraic surface or combined surface is the expected curved surface.

In the embodiments described above, the created curves or curved surface pass through the reference points. In other embodiment, the curves or curved surface may not pass through the reference points, but satisfy some constraint conditions based on the reference points. For example, the distance between the curves or the curved surface and the reference point is a predefined value or meet predefined conditions, e.g., the reference point is the center or focus of the curve, or the reference point is the center or focus of the curved surface, etc. All of these curves or surfaces (including those passing through the reference point and those meeting the constraints conditions) are referred to as curves or surfaces "defined" by the reference points and other points.

In the embodiments described above, the curved surfaces are created on end plane ABCD of the initial frame. In other embodiments, the curved surfaces may also be created on one or at least two other end planes of the initial frame. Alternatively, the curved surfaces may be created on all of the six end planes of the initial frame. Then, the curved surfaces and the other end planes of the initial frame, or, all of the six curved surfaces, may form a closed volume, which is the expected VOI.

In the embodiments described above, the curved surfaces may be created only based on a predefined initial frame and selected reference points. The reference points may be selected arbitrarily based on requirements of imaging, facilitating ease of user operation. If the target of imaging is not located inside the initial frame, the initial frame need not move to make the initial frame contain the target. Reference points only need to be selected to make the created VOI based on the reference points contain the target. Moreover, the number and location of selected reference points are arbitrary. As a result, the VOI may be obtained whose shape is more corresponding to shape of the target by selecting the number and location of the reference points reasonably, by which to reduce background region contained in the VOI.

In the embodiments described above, the simplest way for selecting reference points is that the user directly inputs the coordinates of the reference points. For example, the user may input the x coordinate, y coordinate and z coordinate of reference point into three input boxes supplied by imaging system. In certain embodiments, the coordinates of reference points may also be supplied by imaging system automatically, e.g., using any known edge or boundary detection methods to obtain expected points which will serve as reference points. In other embodiments, reference points may also be selected in other ways, as described below.

Figure 9:
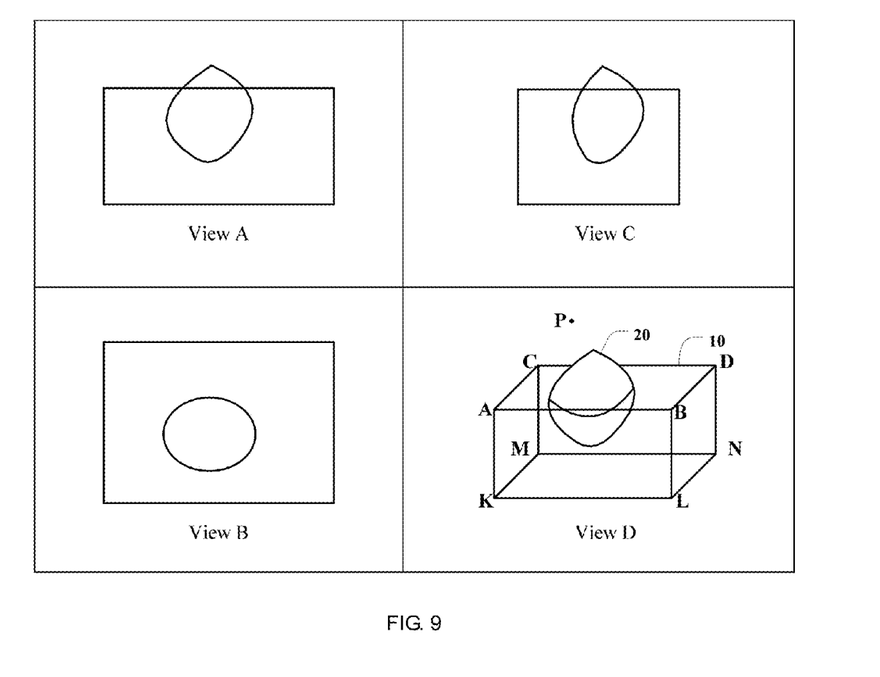
FIG. 9 is a schematic diagram of an embodiment of a display interface of a 3D ultrasound imaging system.

Usually, there are four views on display of imaging system. As shown in FIG. 9, the view A, view B and view C are section views, and the view D is a 3D view. The three section views are mutually perpendicular. On the section views, the corresponding sections of the VOI are also overlaid. If the VOI was cuboid (for example, the initial frame above) and the corresponding end planes were parallel to the section view respectively, then the section of the VOI separately overlaid on the section views is rectangle.

Figure 10:
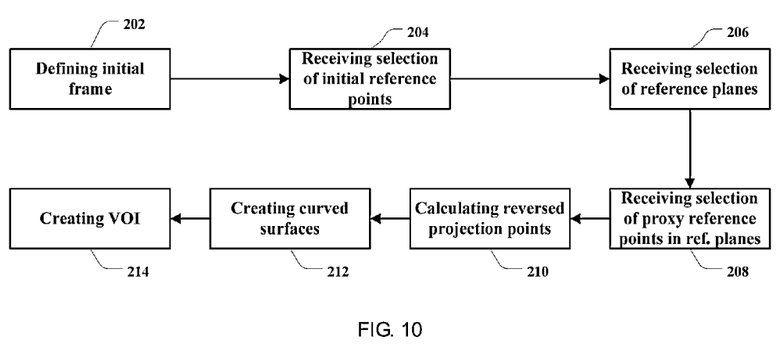
FIG. 10 is a flow diagram of another embodiment of a method of defining a VOI.

FIG. 10 illustrates a method for selecting the reference points and defining VOI including steps 202, 204, 206, 208, 210, 212 and 214. In step 202, an initial frame of the VOI in the ultrasound imaging space is defined. In step 204, selecting signals for selecting an initial reference point are received in order to select at least one initial reference point at an arbitrary location in the imaging space. The selecting signals may be generated by the imaging system automatically or by user input.

In step 206, selecting signals are received for selecting at least one reference plane in the ultrasound imaging space. The selected reference planes may be one or more of the planes of view A, view B and view C in FIG. 9. In certain embodiments, one or more of the other planes may be selected as reference plane(s). In such embodiments, for the convenience of calculation, the section views displayed on the display may be changed to make the section views located on the selected reference planes to be displayed in view A, view B or view C. Similarly, these selecting signals may be generated by the imaging system automatically or by user input.

In step 208, selecting signals are received for a selecting proxy reference point to select at least one proxy reference point at an arbitrary location of the reference plane. The locations of the proxy reference points are not limited. These selecting signals may be generated by the imaging system automatically, such as the imaging system directly gives the coordinates of the proxy reference points. These selecting signals may also be generated by user input, such as the user inputting the coordinates of the proxy reference points, or clicking the mouse to select points which would be proxy reference points in the reference plane. The number of the proxy reference points is not limited and may be one or more.

When the reference planes are selected, the relationship between the initial reference points and the reference planes are determined. As a result, the initial reference points and the reference planes may be corresponded according to certain rules to obtain the corresponding points of the initial reference points in the reference planes. For example, the simplest rule is vertical projection, e.g., projecting vertically the initial reference points to the reference planes. The projection points are the corresponding points. In another embodiment, the initial reference points may be "projected" to the reference planes along oblique lines or curves, e.g., calculating the intersection points of the reference planes and the oblique lines or curves which pass through the initial reference points. The intersection points are the corresponding points. Of course, there may be other rules according to which the initial reference points are corresponded to the reference planes. These rules are referred to herein as a "projection relationship" and the corresponding points are referred to as "projection points".

A person skilled in the art will understand that if the projection relationship and the projection points are known, the initial reference points may be calculated (assuming that the initial reference points were not known) according to a "reversed projection relationship." Similarly, for other points in the reference planes (even if they are not projection points), corresponding points out of the reference planes can also be calculated according to the reversed projection relationship above. These corresponding points calculated by the reversed projection relationship are referred to herein as "reversed projection points".

In various embodiments, the projection relationships are not limited. They may be any relationship which satisfy requirements. The projection relationship to be used may be selected by the imaging system or by the user via the user interface.

Accordingly, after selecting the proxy reference points, in step 210, the reversed projection points of the selected proxy reference points may be calculated. These reversed projection points then are used as the reference points being selected.

Figure 11:
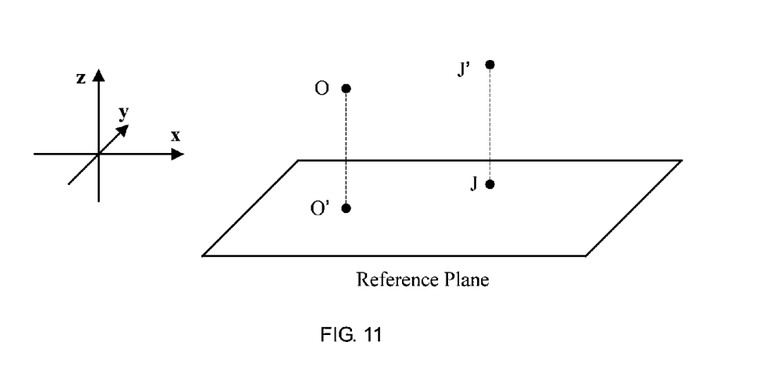
FIG. 11 is a schematic diagram illustrating an embodiment of calculating the reverse projection point of a proxy reference point.

In one embodiment, the projection relationship is vertical projection. As shown in FIG. 11, point O is initial reference point. Point O is projected vertically to the reference plane. Point O' is the projection point. Point J is the selected proxy reference point. Point J is reversely projected. In other words, starting from point J, along the direction that is reversed to the direction from point O to point O', find point J' by making JJ'=OO'. Point J' is the reversed projection point, that is, the reference point.

Assuming the coordinates of the initial reference point O are (x1, y1, z1) and the coordinate of the reference plane is z2, then the coordinates of the projection point O' are (x1, y1, z2). Assuming the x and y coordinates of the selected proxy reference point J are (x2, y2), then the coordinates of point J are (x2, y2, z2) and the coordinates of the reversed projection point J' of the projection point J are (x2, y2, z1). That is, the coordinates of the reference point are (x2, y2, z1).

In another embodiment, the initial reference point is projected to the reference plane along a curve z=g(y) which pass through the initial reference point. For example, the coordinates of the initial reference point are (x2, y2, z2) and the reference plane is y=y3, then the coordinates of the projection point of the initial reference point in the reference plane are (x2, y3, g(y3)). If the coordinates of the selected proxy reference point in the reference plane were (x2', y3, z2'), then the coordinates of the reversed projection point of the proxy reference point are (x2', $g^{-1}$(z2'), z2'), and the function $g^{-1}$( ) is inverse function of function g( ).

If the interim curves and the curved surfaces have been obtained already before and the purpose of selecting proxy reference points is to adjust the curved surfaces obtained (described below), the initial reference points may be projected to the reference plane along the interim curves. As FIG. 7 shows, the initial reference point (solid point in FIG. 7) is projected to the reference plane P1 along interim curve S.

After obtaining the reference points, in step 212, create at least one curved surface using at least one of the reference points and at least one of the elements of the initial frame; In step 214, create the VOI based on the at least one curved surface. In this embodiment, except steps 206, 208 and 210, steps 202, s, 212 and 214 are same or similar with steps 102, 104, 106 and 108 above.

In another embodiment, the proxy reference points may be obtained by moving the projection points of the initial reference points in the reference planes. That is, after selecting the initial reference points, the projection points of the initial reference points in the reference planes may be calculated and displayed, then these projection points may be moved to expected locations using, for example, a mouse. These points in new locations then are used as the proxy reference points.

In another embodiment, the proxy reference points may be adjusted or updated. That is, signals for adjusting or updating the proxy reference points may be received, then the locations of the proxy reference points may be adjusted or updated according to the signals, which may be inputted by the user.

In certain embodiments, the obtained VOI may be "updated" by selecting new proxy reference points in the reference plane and then calculating new reference points using the methods described above. That is, new proxy reference points may be selected, then reference points may be recalculated using the methods described above based on the selected new proxy reference points, the curved surfaces may be recalculated based on the new reference points according to steps 106, 108 or steps 212, 214 described above, and then, the VOI may be redefined based on the recalculated curved surfaces. In this way, the VOI may be adjusted to better satisfy the requirements of the user.

An apparatus using the above-described methods for defining the VOI will be described in detail hereafter.

Figure 12:
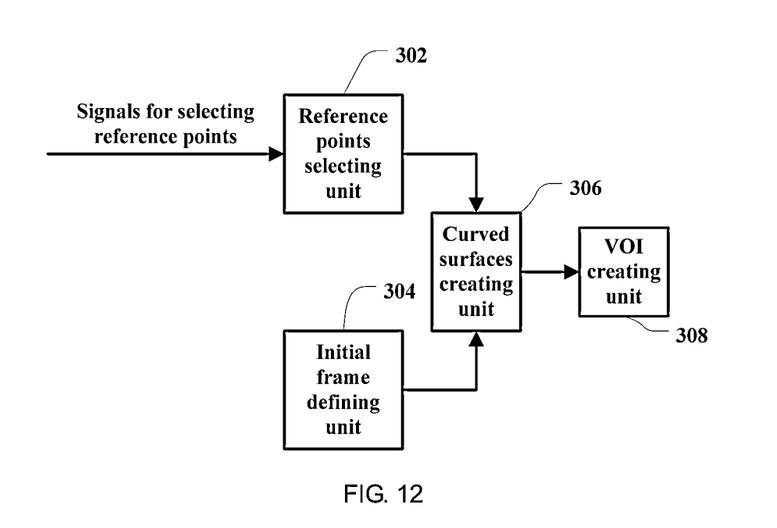
FIG. 12 is a block diagram of an embodiment of an apparatus for defining a VOI.

In one embodiment, the rendering unit of the 3D imaging module for implementing the rendering step in FIG. 2 includes an apparatus for defining the VOI in the ultrasound imaging space. As shown in FIG. 12, the apparatus may include a reference points selecting unit 302, an initial frame defining unit 304, a curved surfaces creating unit 306, and a VOI defining unit 308, wherein the reference points selecting unit 302 and initial frame defining unit 304 are in communication with the curved surfaces creating unit 306, which is in communication with the VOI defining unit 308.

The initial frame defining unit 304 defines the initial frame of the VOI in the ultrasound imaging space. The reference points selecting unit 302 receives the signals for selecting the reference points and selects at least one reference point at an arbitrary location in the ultrasound imaging space according to the signals. The curved surfaces creating unit 306 receives the initial frame defined by the initial frame defining unit 304 and the reference points selected by the reference points selecting unit 302 and creates at least one curved surface based on at least one of the reference points and at least one element of the initial frame. The VOI defining unit 308 receives the curved surfaces created by the curved surfaces creating unit 306 and defines the VOI based on the curved surfaces.

The creating curved surface unit 306 may use the methods of step 106 or step 212 above to create the curved surface. In another embodiment, the creating curved surface unit 306 may include a projection points calculating sub-unit, which calculates the projection points of the reference points on the initial frame along at least two directions; an interim curves creating sub-unit, which creates the curves defined by the reference point and its projection points on the initial frame in each projection directions to obtain at least two interim curves; and/or a curved surfaces creating sub-unit, which creates curved surfaces based on the at least two interim curves.

Figure 13:
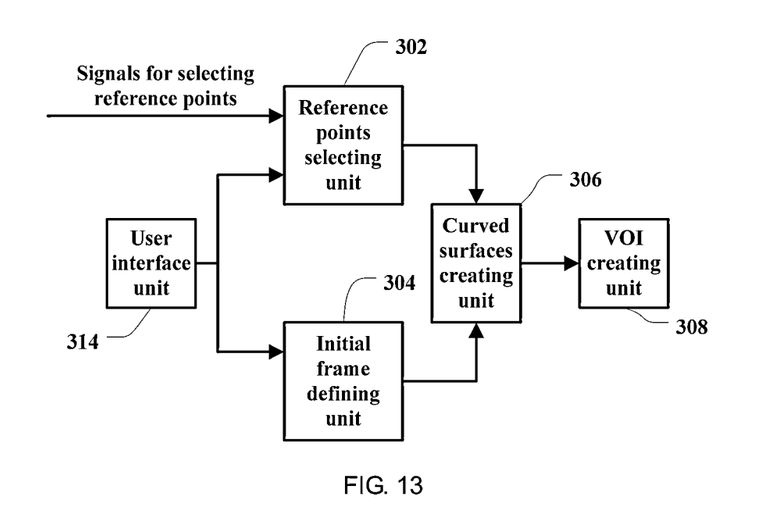
FIG. 13 is a block diagram of another embodiment of an apparatus for defining a VOI.

In another embodiment, the apparatus may further include a user interface unit 314, as shown in FIG. 13. The user interface unit 314 is in communication with at least one of the reference points selecting unit 302 and the initial frame defining unit 304. The user interface unit 314 may also be connected to the display unit 312. As a result, the user can select or adjust the reference points and/or the initial frame of the VOI by the user interface unit 314.

Figure 14:
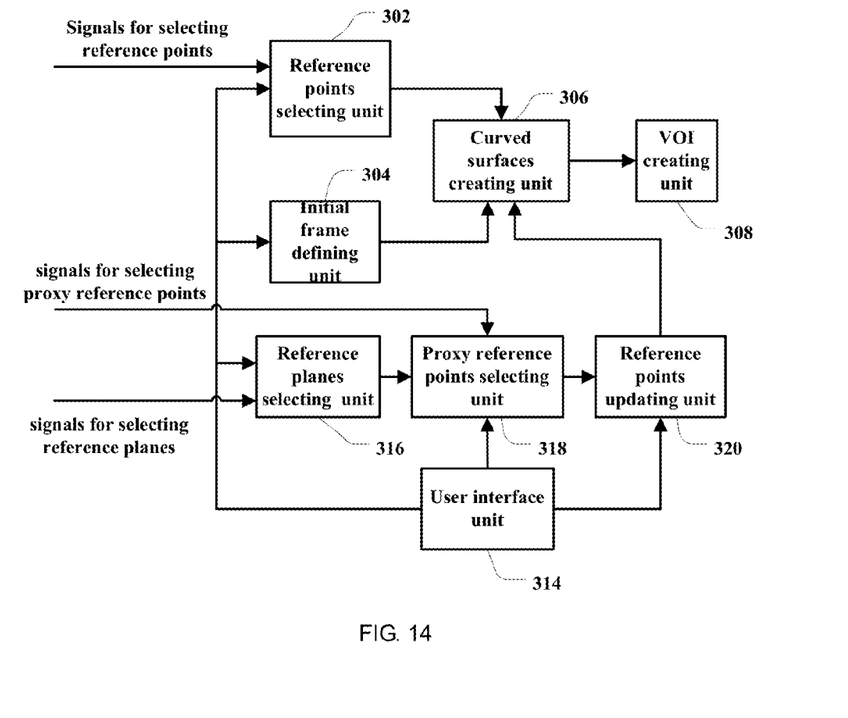
FIG. 14 is a block diagram of a further embodiment of an apparatus for defining a VOI.

In one embodiment, the apparatus may further include a reference planes selecting unit 316, a proxy reference points selecting unit 318, and a reference points updating unit 320, as shown in FIG. 14. The reference planes selecting unit 316 is in communication with the proxy reference points selecting unit 318, which is in communication with the reference points updating unit 320. The reference points updating unit 320 is in communication with the creating curved surface unit 306.

The selecting reference plane unit 316 receives the signals for selecting the reference planes and selects at least one reference plane in the ultrasound imaging space according to these signals. The proxy reference points selecting unit 318 receives the signals for selecting the proxy reference points and selects at least one proxy reference point in the arbitrary location of the reference plane according to these signals. The reference points updating unit 320 calculates the reversed projection points of the proxy reference points selected by the proxy reference points selecting unit 318 according to the "reversed projection relationship" which is reversed to the projection relationship according to which the reference points selected by the reference points selecting unit 302 are projected to the reference plane. Then, the calculated reversed projection points are the new reference points. Correspondingly, the reference points selected by the reference points selecting unit 302 are referred to herein as "initial reference points," and the reference points selecting unit 302 may be referred to as the "selecting initial reference points unit".

The signals for selecting the proxy reference points received by the proxy reference points selecting unit 318 may come from the imaging system or user input.

In one embodiment, the proxy reference points selecting unit 318 may include a projection points calculating sub-unit, which calculates at least one projection point of the reference points in the reference planes; and a projection points moving sub-unit, which receives the signals for selecting proxy reference points and moves the projection points according to this signals. The moved projection points are the proxy reference points. The signals received by the projection points moving sub-unit may come from the imaging system or input of the user (for example, dragging the projection points by a mouse).

In one embodiment, the proxy reference points selecting unit 318 may further include a displaying projection points sub-unit, which displays the calculated projection points.

The user interface unit 314 may be in communication with at least one of the reference points selecting unit 302, the initial frame defining unit 304, the selecting reference plane unit 316, the proxy reference points selecting unit 318, and the reference points updating unit 320. Accordingly, the user can select or adjust the reference points, the initial reference points, the reference plane, the proxy reference points or the initial frame, etc., through the user interface.

The units or sub-units of the apparatus described above work according to the methods described in the above-described embodiments and will not be described in detail again.

In the description above, numerous specific details are provided for a thorough understanding of the embodiments described herein. However, those of skill in the art will recognize that one or more of the specific details may be omitted, or other methods, components, or materials may be used. In some cases, operations are not shown or described in detail.

Furthermore, the described features, operations, or characteristics may be combined in any suitable manner in one or more embodiments. It will also be readily understood that the order of the steps or actions of the methods described in connection with the embodiments disclosed may be changed as would be apparent to those skilled in the art. Thus, any order in the drawings or Detailed Description is for illustrative purposes only and is not meant to imply a required order, unless specified to require an order.

Embodiments may include various steps, which may be embodied in machine-executable instructions to be executed by a general-purpose or special-purpose computer (or other electronic device). Alternatively, the steps may be performed by hardware components that include specific logic for performing the steps or by a combination of hardware, software, and/or firmware.

Embodiments may also be provided as a computer program product including a machine-readable medium having stored thereon instructions that may be used to program a computer (or other electronic device) to perform processes described herein. The machine-readable medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of media/machine-readable medium suitable for storing electronic instructions.

Those of skill in the art would further appreciate that the various illustrative logical blocks, modules, circuits, and algorithm steps described in connection with the embodiments disclosed herein may be implemented as electronic hardware, computer software, or combinations of both. To illustrate the interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the invention as claimed hereinafter.

What is claimed is:

1. A method for defining a volume of interest (VOI) in an ultrasound imaging space, wherein the VOI is used in generating a three-dimensional image, the method comprising:
   defining an initial frame of the VOI in the ultrasound imaging space;
   receiving a selection of at least one reference point at an arbitrary location in the ultrasound imaging space, wherein receiving a selection of at least one reference point further comprises:
      receiving a selection of at least one reference plane in the ultrasound imaging space;
      receiving a selection of at least one proxy reference point in the reference planes; and
      updating the reference points using reversed projection points of the proxy reference points, wherein the reversed projection points are obtained by projecting the proxy reference points according to a reversed projection relationship which is reversed to the projection relationship according to which the reference points are projected to the reference planes;
   creating at least one curved surface using at least one element of the initial frame and the at least one reference point; and
   creating the VOI based on the curved surface in the ultrasound imaging space.

2. The method of claim 1, wherein receiving a selection of at least one proxy reference point comprises:
   calculating projection points of the reference points in the reference planes; and
   moving the projection points to expected locations in the reference planes, wherein the moved projection points are the proxy reference points.

3. The method of claim 1, wherein receiving a selection of at least one proxy reference point further comprises:
   updating the proxy reference points by moving the proxy reference points or selecting new proxy reference points.

4. The method of claim 1, wherein creating the curved surface comprises:
   calculating an algebraic surface defined by at least one element of the initial frame and the at least one reference point.

5. The method of claim 1, wherein creating the curved surface comprises:
   calculating projection points of the reference points in the initial frame along at least two directions;
   calculating curves defined by the reference points and the projection points along each direction respectively to obtain at least two interim curves; and
   creating synthesized curved surfaces based on at least two of the interim curves.

6. The method of claim 5, wherein calculating the interim curves comprises:
   calculating algebraic curves which employ the at least one reference point as the vertex and pass through one or more projection points of the at least one reference point in the initial frame along each direction respectively.

7. The method of claim 5, wherein calculating the interim curves comprises:
   calculating curves which include at least two sub-curves, wherein each of the sub-curves starts from the at least one reference point and pass through one or more projection points of the at least one reference point in the initial frame along each direction respectively.

8. A method for defining a volume of interest (VOI) in an ultrasound imaging space, wherein the VOI is used in generating a three-dimensional image, the method comprising:
   defining an initial frame of the VOI in the ultrasound imaging space;
   receiving a selection of at least one initial reference point at an arbitrary location in the ultrasound imaging space;
   receiving a selection of at least one reference plane in the ultrasound imaging space;
   receiving a selection of at least one proxy reference point in the reference plane;
   calculating reversed projection points of the proxy reference points, wherein the reversed projection points are obtained by projecting the proxy reference points according to a reversed projection relationship which is reversed to the projection relationship according to which the reference points are projected to the reference planes, wherein the reversed projection points are reference points;
   creating at least one curved surface using at least one element of the initial frame and the at least one reference point; and
   creating VOI based on the curved surface.

9. An apparatus for defining a volume of interest (VOI) in an ultrasound imaging space within ultrasound imaging system comprising:
   a probe;
   a signal processing module and;
   a 3D imaging module, wherein the 3D imaging module comprises a processor configured to:
      define an initial frame of the VOI in the ultrasound imaging space;
      receive a selection of at least one reference point at an arbitrary location in the ultrasound imaging space;
      create at least one curved surface using at least one element of the initial frame and the at least one reference point; and
      create the VOI based on the curved surface in the ultrasound imaging space;
      receive a selection of at least one reference plane in the ultrasound imaging space;
      receive a selection of at least one proxy reference point in the reference planes;
      update the reference points using reversed projection points of the proxy reference points, wherein the reversed prosection points are obtained by projecting the proxy reference points according to a reversed projection relationship which is reversed to the projection relationship according to which the reference points are projected to the reference planes.

10. The apparatus of claim 9, wherein the apparatus further comprises:
    a user interface which is in communication with the 3D imaging module.

11. The apparatus of claim 9, wherein the processor is further configured to:
    calculate projection points of the reference points in the reference planes;

move the projection points to expected locations in the reference planes and the moved projection points are the proxy reference points.

12. The apparatus of claim 9, wherein the processor is further configured to:
   calculate projection points of the reference points in the initial frame along at least two directions;
   calculate curves defined by the reference points and the projection points along each direction respectively to obtain at least two interim curves; and
   create synthesized curved surfaces based on at least two of the interim curves.

13. An apparatus for defining a volume of interest (VOI) in an ultrasound imaging space within an ultrasound imaging system comprising:
   a probe;
   a signal processing module; and
   a 3D imaging module, the 3D imaging module comprising a processor configured to:
      define an initial frame of the VOI in the ultrasound imaging space;
      receive a selection of at least one reference point at an arbitrary location in the ultrasound imaging space;
      receive a selection of at least one reference plane in the ultrasound imaging space;
      receive a selection of at least one proxy reference point in the reference planes;
      update the reference points using reversed projection points of the proxy reference points, wherein the reversed projection points are obtained by projecting the proxy reference points according to a reversed projection relationship which is reversed to the projection relationship according to which the reference points are projected to the reference planes;
      create at least one curved surface using at least one element of the initial frame and at the least one reference point; and
      create the VOI based on the curved surface in the ultrasound imaging space.

14. A non-transitory computer-readable medium comprising program code for causing a computer to perform a method for defining a volume of interest (VOI) in an ultrasound imaging space, wherein the VOI is used in generating a three-dimensional image, the method comprising:
   defining an initial frame of the VOI in the ultrasound imaging space;
   receiving a selection of at least one reference point at an arbitrary location in the ultrasound imaging space;
   creating at least one curved surface using at least one element of the initial frame and the at least one reference point; and
   creating the VOI based on the curved surface in the ultrasound imaging space.

15. A method for defining a volume of interest (VOI) in an ultrasound imaging space, wherein the VOI is used in generating a three-dimensional image, the method comprising:
   defining an initial frame of the VOI in the ultrasound imaging space;
   receiving a selection of at least one reference point at an arbitrary location in the ultrasound imaging space;
   creating at least one curved surface using at least one element of the initial frame and the at least one reference point, wherein creating the curved surface comprises:
      calculating projection points of the reference points in the initial frame along at least two directions;
      calculating curves defined by the reference points and the projection points along each direction respectively to obtain at least two interim curves; and
      creating synthesized curved surfaces based on at least two of the interim curves; and
   creating the VOI based on the curved surface in the ultrasound imaging space.

16. An apparatus for defining a volume of interest (VOI) in an ultrasound imaging space within ultrasound imaging system comprising:
   a probe;
   a signal processing module and;
   a 3D imaging module, wherein the 3D imaging module comprises a processor configured to:
      define an initial frame of the VOI in the ultrasound imaging space;
      receive a selection of at least one reference point at an arbitrary location in the ultrasound imaging space;
      create at least one curved surface using at least one element of the initial frame and the at least one reference point; and
      create the VOI based on the curved surface in the ultrasound imaging space;
      calculate projection points of the reference points in the initial frame along at least two directions;
      calculate curves defined by the reference points and the projection points along each direction respectively to obtain at least two interim curves; and
      create synthesized curved surfaces based on at least two of the interim curves.

* * * * *